(12) United States Patent
Quinn

(10) Patent No.: US 9,044,147 B2
(45) Date of Patent: Jun. 2, 2015

(54) DETECTION OF NOISE DURING HEART BEAT VARIATION EVALUATION

(75) Inventor: David E. Quinn, Auburn, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 687 days.

(21) Appl. No.: 13/162,621

(22) Filed: Jun. 17, 2011

(65) Prior Publication Data
US 2011/0313300 A1 Dec. 22, 2011

Related U.S. Application Data

(60) Provisional application No. 61/355,919, filed on Jun. 17, 2010, provisional application No. 61/418,186, filed on Nov. 30, 2010.

(51) Int. Cl.
A61B 5/02 (2006.01)
A61B 5/022 (2006.01)

(52) U.S. Cl.
CPC .................................. A61B 5/02225 (2013.01)

(58) Field of Classification Search
USPC .......................................................... 600/485
See application file for complete search history.

(56) References Cited

U.S. PATENT DOCUMENTS

| 4,356,827 | A | 11/1982 | Uemura et al. |
| 4,860,759 | A | 8/1989 | Kahn et al. |
| 5,680,867 | A | 10/1997 | Shimazu et al. |
| 6,050,951 | A | 4/2000 | Friedman et al. |
| 6,423,010 | B1 | 7/2002 | Friedman et al. |
| 6,485,429 | B2 | 11/2002 | Forstner |
| 6,519,490 | B1 | 2/2003 | Wiesel |
| 7,283,870 | B2 | 10/2007 | Kaiser et al. |
| 7,341,560 | B2 | 3/2008 | Henderson et al. |
| 7,353,127 | B2 | 4/2008 | Navakatikyan et al. |
| 7,390,303 | B2 | 6/2008 | Dafni |
| 7,691,068 | B2 | 4/2010 | Felder et al. |
| 7,706,868 | B2 | 4/2010 | Wiesel |
| 2001/0037068 | A1* | 11/2001 | Goto et al. .................. 600/485 |
| 2002/0120199 | A1* | 8/2002 | Ogura et al. ................ 600/485 |
| 2002/0183627 | A1 | 12/2002 | Nishii et al. |
| 2004/0236187 | A1 | 11/2004 | Bock et al. |
| 2005/0171447 | A1 | 8/2005 | Esperer |
| 2005/0187481 | A1 | 8/2005 | Hatib et al. |
| 2005/0261597 | A1 | 11/2005 | Kolluri et al. |
| 2005/0283086 | A1 | 12/2005 | Satoh et al. |

(Continued)

FOREIGN PATENT DOCUMENTS

| EP | 960598 | 12/1999 |
| EP | 841034 | 8/2003 |

OTHER PUBLICATIONS

International Search Report and Written Opinion in PCT/US2011/040813 mailed Feb. 9, 2012, 9 pages.

(Continued)

Primary Examiner — Michael Kahelin
Assistant Examiner — Mitchell E Alter
(74) Attorney, Agent, or Firm — Merchant & Gould P.C.

(57) ABSTRACT

A medical device obtains an oscillometric measurement associated with a patient's non-invasive blood pressure reading. The device determines a stability measure for at least one pair of pulses included in the oscillometric measurement, compares the stability measure to a threshold, and excludes the pair of pulses from an evaluation of heart beat variation when the stability measure fails to meet the threshold.

18 Claims, 9 Drawing Sheets

(56) References Cited

U.S. PATENT DOCUMENTS

| | | | |
|---|---|---|---|
| 2006/0079773 | A1 | 4/2006 | Mourad et al. |
| 2006/0195035 | A1* | 8/2006 | Sun .............................. 600/503 |
| 2007/0021678 | A1 | 1/2007 | Beck et al. |
| 2007/0232939 | A1 | 10/2007 | Forstner |
| 2008/0208064 | A1 | 8/2008 | Lee |
| 2008/0214941 | A1 | 9/2008 | Lin |
| 2008/0262364 | A1 | 10/2008 | Aarts |
| 2008/0287811 | A1 | 11/2008 | Nesterov et al. |
| 2009/0012412 | A1 | 1/2009 | Wiesel |
| 2009/0043179 | A1 | 2/2009 | Melker et al. |
| 2009/0281838 | A1 | 11/2009 | Lynn et al. |
| 2009/0326353 | A1 | 12/2009 | Watson et al. |
| 2010/0076326 | A1 | 3/2010 | Cohen et al. |
| 2010/0280396 | A1* | 11/2010 | Zhang ........................... 600/485 |
| 2011/0313301 | A1 | 12/2011 | Lane et al. |

OTHER PUBLICATIONS

International Search Report and Written Opinion in PCT/US2011/040815 mailed Feb. 9, 2012, 10 pages.

A Singapore-invented Portable Blood-Pressure-Monitoring Device's Innovative Technology with the Potential to Prevent a Sudden Heart Attack or Stroke Has Attracted the Attention of the World Economic Forum, as Well as Kings and Heads of States; Accessed via: http://www.innovationmagazine.com/innovation/volumes/v7n3/feature2.shtml; 5 pgs, Copyright 2011.

Cooke et al.: Is Pulse Palpation Helpful in Detecting Atrial Fibrillation?; The Journal of Family Practice, vol. 55, No. 2, Feb. 2006; pp. 130-134.

Forstner: Pulse Arrhythmia Diagnosis by Oscillometric Blood Pressure Measurement; American Journal of Hypertension, vol. 16, Issue 5, Supplement 1, May 2003, p. 48A.

Huang et al: Accuracy of Automated Oscillometric Blood Pressure Monitors in the Detection of Cardiac Arrhythmias; Blood Pressure Monitoring 2009, vol. 14, No. 2; pp. 91-92, Apr. 2009.

Microlife PAD Technology; Accessed via: http://www.padtechnology.net/; 1 pg, Jan. 2008.

O'Brien et al: Heart Rate Variability in Healthy Subjects: Effect of Age and the Derivation of Normal Ranges for Tests of Autonomic Function; Deparment of Medicine, Bristol Royal Infirmary, Bristol BS2 8HW; Accepted for publication Dec. 17, 1985; pp. 348-354.

Ohira et al.: Associations of Psychosocial Factors With Heart Rate and Its Short-Term Variability: Multi-Ethnic Study of Atherosclerosis; Psychosomatic Medicine, Copyright © 2008 by the American Psychosomatic Society; pp. 141-146, Mar. 2008.

Omron HEM-650 Wrist Blood Pressure Monitor with APS (Advanced Positioning Sensor); Accessed via: http://www.amazon.com/dp/B000FK1V2Q; 7 pgs, Jun. 2007.

Pinheiro et al.: Heart Rate Variability Virtual Sensor Application in Blood Pressure Assessment System; Proceedings of the Sixth IASTED International Conference; Biomedical Engineering, Feb. 13-15, 2008, Innsbruck, Austria; pp. 79-82.

Stergiou et al.: Diagnostic Accuracy of a Home Blood Pressure Monitor to Detect Atrial Fibrillation; Hypertension Center, Third University Department of Medicine, Sotiria Hospital, Athens, Greece; Journal of Human Hypertension, Feb. 12, 2009; © 2009 Macmillan Publishers Limited; pp. 654-658.

* cited by examiner

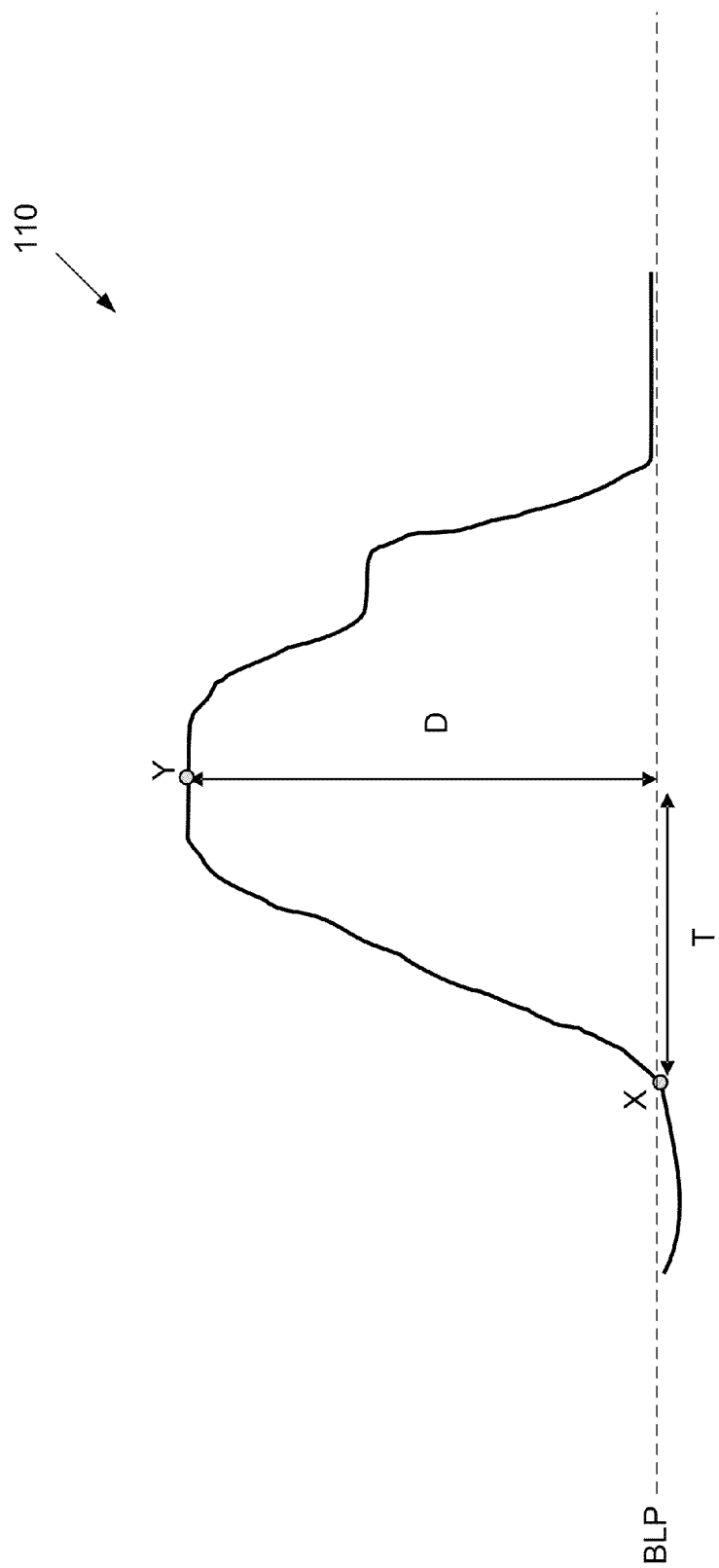

DETECTION OF NOISE DURING HEART BEAT VARIATION EVALUATION

RELATED APPLICATIONS

This application claims the benefit of U.S. Patent Application Ser. No. 61/355,919 filed on Jun. 17, 2010 and U.S. Patent Application Ser. No. 61/418,186 filed on Nov. 30, 2010, the entireties of which are hereby incorporated by reference.

BACKGROUND

A sphygmomanometer can be used to measure a patient's blood pressure in a non-invasive manner. In a typical example, a cuff is placed around the patient's arm and inflated. The cuff is deflated, and the blood starts to flow within the arm again. By monitoring the pressures at which the blood starts to flow (i.e., the maximum output pressure or systolic reading) and the pressure upon relaxation (i.e., the diastolic reading), an estimate of the patient's blood pressure readings can be obtained. Throughout the deflation of the cuff, arterial pressure changes cause pulsations or oscillations in the cuff pressure which have a correlation to the changing blood pressure in the underlying artery during a heart cycle.

SUMMARY

Embodiments of the present disclosure are directed to systems and methods for detecting noise during heart beat variation evaluation.

In one aspect, a medical device includes: a central processing unit (CPU) that is configured to control operation of the device; and a set of one or more computer readable data storage media storing software instructions that, when executed by the CPU, cause the device to: obtain an oscillometric measurement associated with a patient's non-invasive blood pressure reading; determine a stability measure for at least one pair of pulses included in the oscillometric measurement; compare the stability measure to a threshold; and exclude the pair of pulses from an evaluation of heart beat variation when the stability measure fails to meet the threshold.

In another aspect, a method for estimating noise associated with an evaluation of heart beat variation includes: obtaining an oscillometric measurement associated with a patient's non-invasive blood pressure reading; determining a stability measure for at least one pair of pulses included in the oscillometric measurement; comparing the stability measure to a threshold; and determining when the stability measure fails to meet the threshold.

In yet another aspect, a method for estimating noise associated with an evaluation of heart beat height variation includes: obtaining an oscillometric measurement associated with a patient's non-invasive blood pressure reading; selecting at least one pair of pulses included in the oscillometric measurement; calculating an average of a peak pressure of each pulse in the pair of pulses; calculating a difference in a starting pressure at a start of each pulse in the pair of pulses; comparing the average to the difference to define a stability ratio; comparing the stability ratio to a threshold; and determining when the stability ratio fails to meet the threshold; excluding the pair of pulses when the stability ratio exceeds the threshold; and alerting a user when the pair of pulses is excluded from the evaluation of heart beat height variation.

DESCRIPTION OF THE DRAWINGS

The present disclosure can be better understood with reference to the description below. Within the drawings, like reference numbers are used to indicate like parts throughout the various views. Differences between like parts may cause those like parts to be each indicated by different reference numbers. Unlike parts are indicated by different reference numbers.

FIG. 2 shows a single pulse from the oscillometric signal of FIG. 1.

DETAILED DESCRIPTION

Embodiments of the present disclosure are directed to systems and methods for detecting noise during heart beat variation evaluation.

It is possible to perform an assessment of heart beat variation using the oscillometric signal from a blood pressure cuff. Heart beat variation can be evaluated by analyzing the oscillometric pulses and comparing their time regularity and height regularity. The oscillometric signal contains information related to the amount of blood pressure and flow in the peripheral arteries. This indication can be important, as the resulting blood flow from heart activity is the most critical aspect of the cardiac cycle.

Heart beat variation in the oscillometric signal can be evaluated by combining the pulse timing interval and the relative pulse heights of subsequent or groups of pulses. In this aspect, evaluating the oscillometric waveform can provide information that is more directly related to cardiac output than other information, such as information from an electrocardiogram.

When taking the oscillometric measurements, ideally the pressure in the cuff is stable. When an arterial pulse does occur, the pulse adds to the baseline pressure in the cuff. The pressure returns to the baseline pressure when the impact of the pulse has dissipated. This cycle continues for each pulse.

When artifact noise is introduced into the system, it can be difficult to distinguish between the changes in pressure caused by the underlying artery and those caused by the noise. Tracking the stability and consistency of this baseline pressure allows the detection of artifact noise and pulse altering changes in the cuff pressure that are not due to cardiogenic pulsations in the artery. Noise can also alter the morphology and amplitude of a given pulse.

In examples described herein, the oscillometric blood pressure signal is analyzed to allow differentiation between heart beat variation that is real and signal disturbances that are due to artifact noise, such as arm movement, muscle flexing or other cuff disturbances. It can be desirable to identify measurements impacted by artifact noise so that false indications of heart beat variation are minimized.

Figure 1:
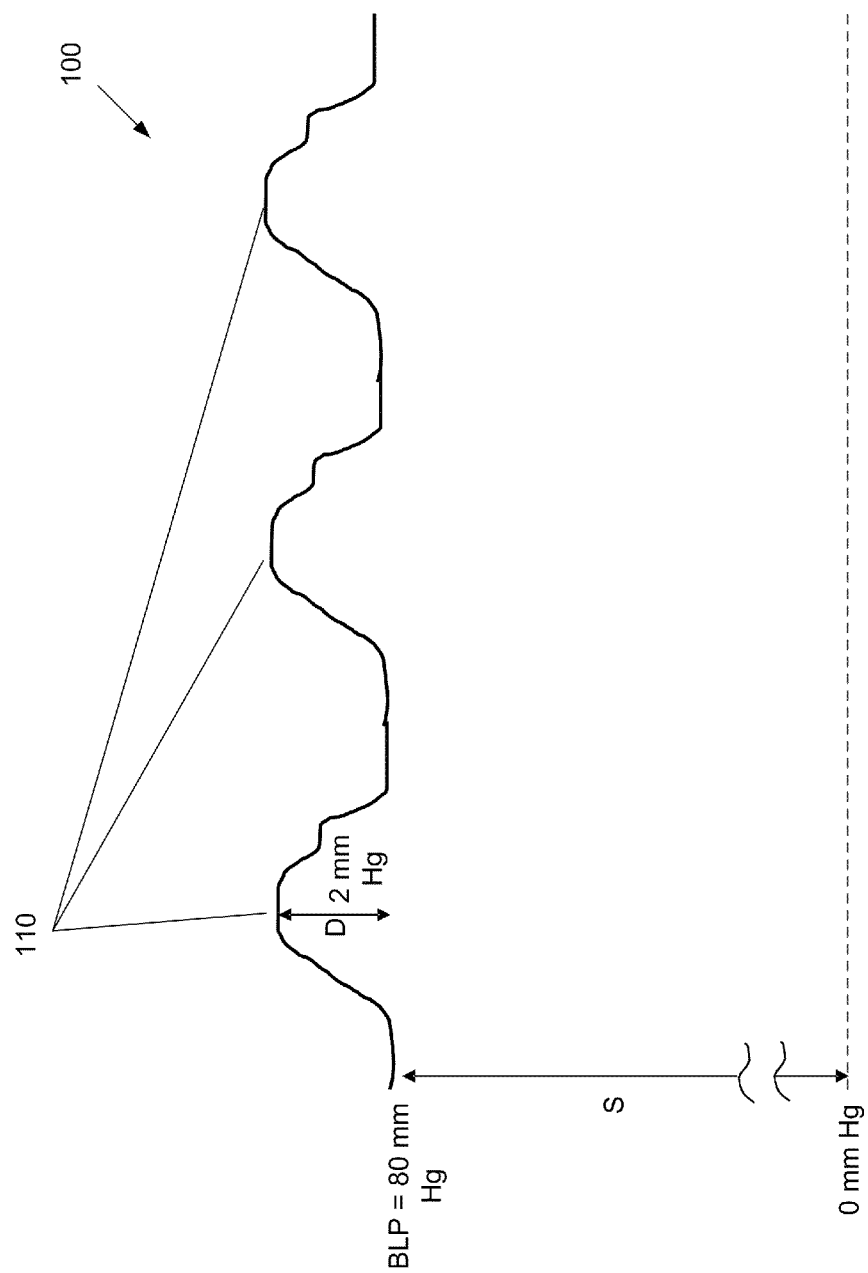
FIG. 1 shows an example oscillometric signal associated with an individual's blood pressure.

FIG. 1 illustrates an oscillometric signal 100 as measured by a blood pressure device. The oscillometric signal 100 shows the measured pressures associated with the movement of blood through the patient's body, typically an arm. Specifically, three pulses 110 are the variations in cuff pressure caused by changes in pressure within the underlying artery.

The oscillometric signal 100 in the cuff is made up of a static component S (the baseline pressure pumped into the cuff) and a dynamic component D (induced into the cuff by blood moving through the underlying artery). These two components are summed together to result in an amplitude of the oscillometric signal 100.

For example, the oscillometric signal 100 shown in FIG. 1 includes the three pulses 110, each with an approximate peak of 82 mm Hg (i.e., 80 mm Hg baseline pressure (BLP) plus 2 mm Hg pulse pressure (height D) attributable to the movement of blood through the patient's arteries).

FIG. 2 illustrates one of the pulses 110 in more detail.

In this example, the peak height D is used to determine the blood pressure value and is compared from pulse to pulse as an indication of pulse height regularity. Since the pulse 110 has a rising slope, there is a natural time delay T between a starting point X of the pulse 110 and a peak point Y of the pulse 110.

In an ideal measurement, a stabile static BLP is provided in the cuff during time T so that the only significant contributing factor to the pulse height D is the dynamic element of the pressure waveform caused by the blood flowing in the artery.

One or more algorithms are used to detect the starting point X at which the pulse 110 starts and the peak point Y where the pulse 110 reaches a peak. Examples of such algorithms to identify point X include detection of the rising inflection point at X where the increase in slope (first derivative) is at a local maximum value indicating a rapid departure from the static pressure. Examples of such algorithms to identify point Y include detection of the point at which the rising slope becomes a falling slope in a given period of time after X. This reversal of slope indicates a peak point which is identified as point Y for this pulse.

The pulse height D can be determined by subtracting the pressure at the starting point X from the pressure at the peak point Y. This calculation assumes that the static BLP is stable. In example embodiments, this pulse height D can be compared between consecutive pulses 110 to evaluate pulse height variability. Pulse height variability indicates relative variability in the cardiac cycle from one heart beat to the next.

Figures 2B, 3:
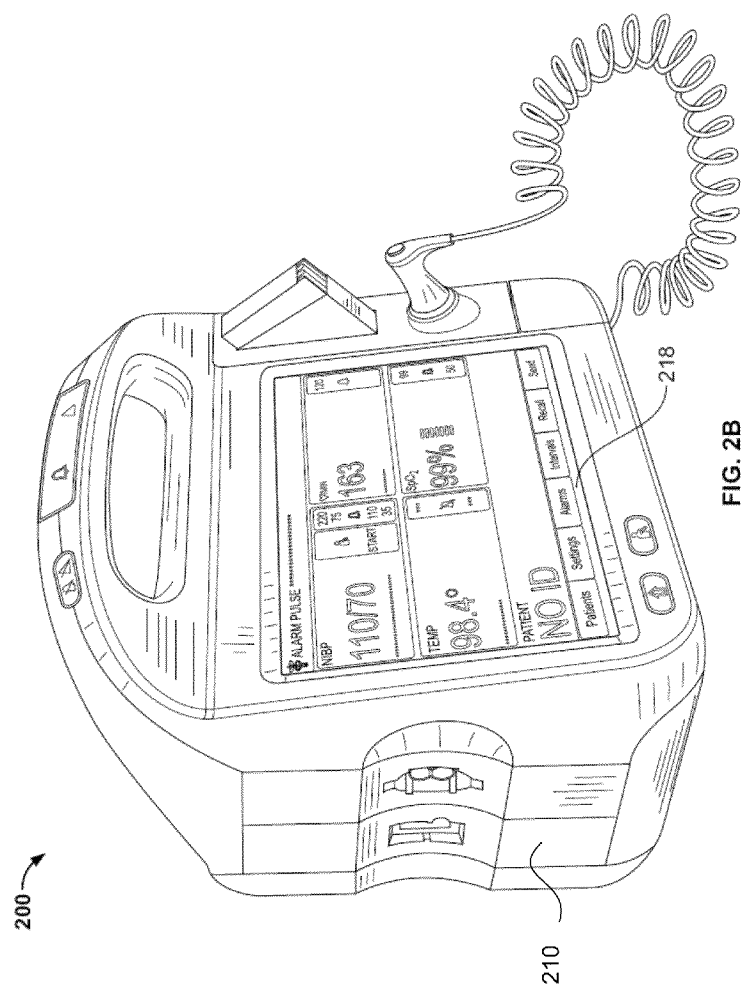
FIG. 3 shows an example physiological monitor device.

FIG. 3 illustrates an example physiological monitor device 200. The device 200 generally assists a caregiver in gathering data associated with a patient, such as vital signs, etc. For example, in embodiments described herein, the physiological monitor device 200 is configured to capture the oscillometric signal 100. In some examples, the physiological monitor device 200 is also configured to interpret the patient's blood pressure reading and to identify potential heart irregularities, such as heart beat height variation.

In the example shown, the physiological monitor device 200 includes multiple health care equipment (HCE) modules 210. Each of the HCE modules 210 is configured to measure one or more physiological parameters of the patient. Example modules include a temperature measurement module, an SpO2 module, and a non-invasive blood pressure (NIBP) module.

The NIBP module connects to one or more peripheral NIBP components, such as an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

A front side of the physiological monitor device 200 includes a display screen 218. The display screen 218 is used to display physiological measure data obtained from the patient. For example, the patient's blood pressure and pulse rate can be displayed on the display screen 218. In another example, the oscillometric signal 100 can be displayed. In addition, data associated with the irregularities detected using the NIBP data can be displayed on the display screen 218. For example, the physiological monitor device 200 can display a warning if a heart beat height variation is detected in the oscillometric signal 100. In addition, the physiological monitor device 200 can display an error message if noise has impacted the detection of the oscillometric signal 100.

Figure 4:
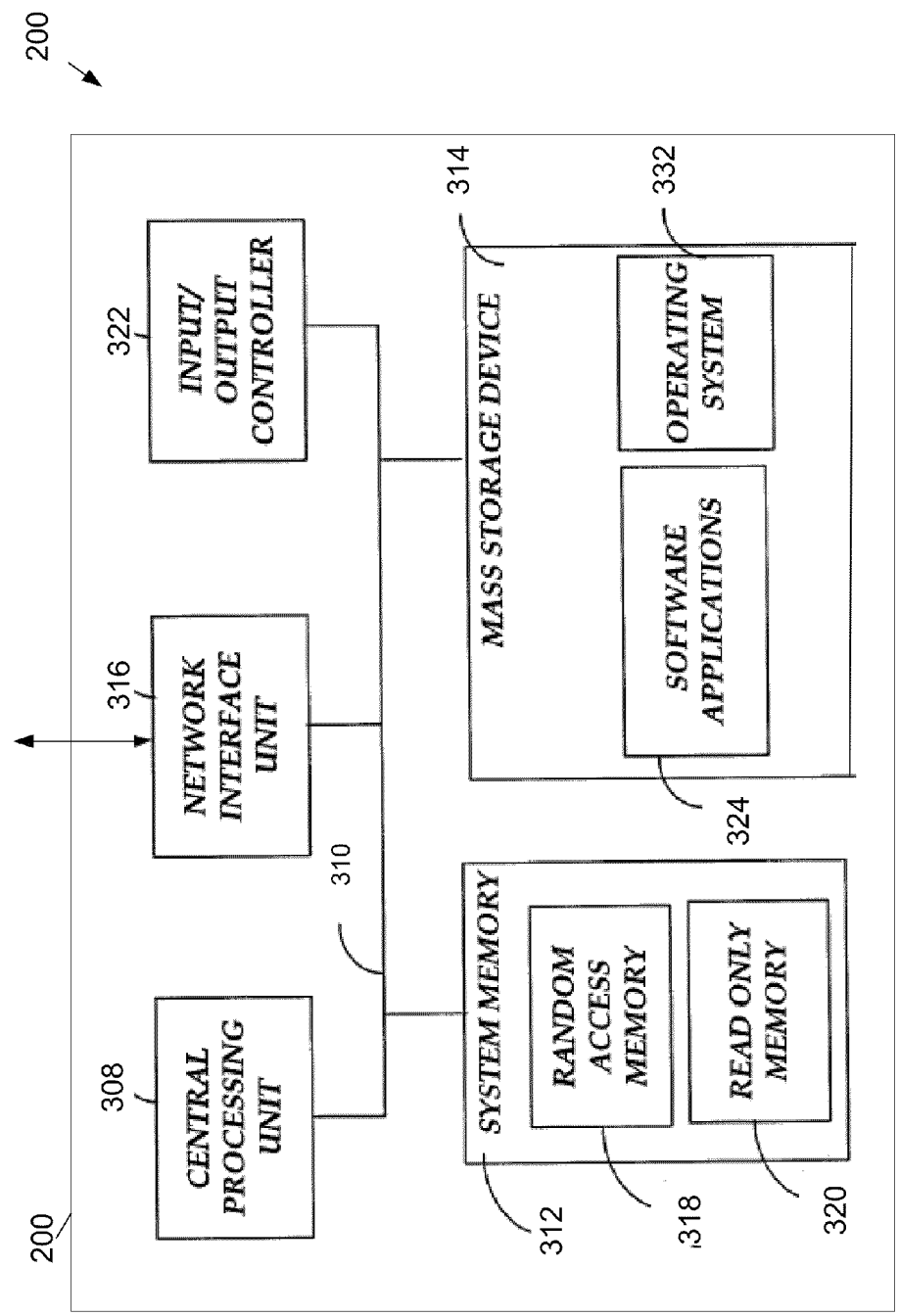
FIG. 4 shows example physical components of the device of FIG. 2.

FIG. 4 illustrates example physical components of the physiological monitor device 200. As illustrated, the physiological monitor device 200 include at least one processor or central processing unit ("CPU") 308, a system memory 312, and a system bus 310 that couples the system memory 312 to the CPU 308. The system memory 312 includes a random access memory ("RAM") 318 and a read-only memory ("ROM") 320. A basic input/output system containing the basic routines that help to transfer information between elements within the physiological monitor device 200, such as during startup, is stored in the ROM 320. The physiological monitor device 200 further includes a mass storage device 314. The mass storage device 314 stores software instructions and data.

The mass storage device 314 is connected to the CPU 308 through a mass storage controller (not shown) connected to the system bus 310. The mass storage device 314 and its associated computer-readable data storage media provide non-volatile, non-transitory storage for the physiological monitor device 200. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the physiological monitor device 200 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the physiological monitor device 200.

The physiological monitor device 200 also includes an input/output controller 322 for receiving and processing input from a number of other devices, including a keyboard, a mouse, a touch user interface display screen, or another type of input device. Similarly, the input/output controller 322 may provide output to a touch user interface display screen, a printer, or other type of output device.

As mentioned above, the mass storage device 314 and the RAM 318 of the physiological monitor device 200 can store software instructions and data. The software instructions include an operating system 332 suitable for controlling the operation of the physiological monitor device 200. The mass storage device 314 and/or the RAM 318 also store software instructions, that when executed by the CPU 308, cause the physiological monitor device 200 to provide the functionality of the physiological monitor device 200 discussed in this document. For example, the mass storage device 314 and/or the RAM 318 can store software instructions that, when executed by the CPU 308, cause the physiological monitor device to display information to the caregiver.

In examples described herein, the physiological monitor device 200 can be used to obtain an oscillometric signal associated with an NIBP cycle.

Figure 5:
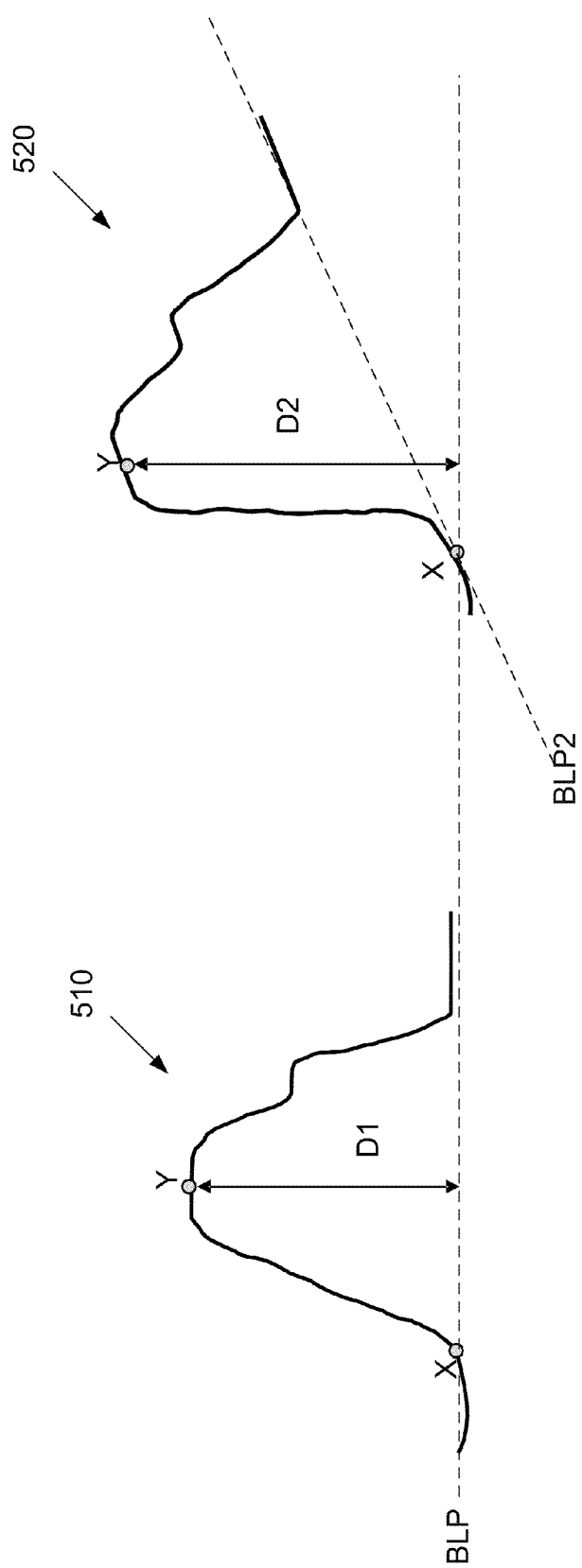
FIG. 5 shows two example pulses from an oscillometric signal.

In one example shown in FIG. 5, the oscillometric signal includes one or more pulses 510, 520 associated with the beating of the patient's heart. As illustrated, a problem can occur with the oscillometric measurement when the static BLP is not stable due to artifact noise that is introduced when the signal is measured. For example, the pulse 510 exhibits a stable BLP, similar to the pulses 110 shown in FIGS. 1 and 2. However, the pulse 520 illustrates a baseline pressure BLP2 that is rising at a significant rate during the course of the measurement during to artifact noise.

The absolute values for the pulse heights for the pulses 510, 520 are approximately the same. However, as a result of the BLP shift, a measured pulse height D1 for the pulse 510 is significantly smaller than a pulse height D2 measured for the pulse 520. An algorithm that evaluates the pulses 510, 520 and assumes a stable BLP could incorrectly determine that there was significant pulse height variability because of the measured height differences between D1 and D2.

As described further below, example embodiments disclosed herein are used to categorize the amount of BLP change by comparing the pressure values of the pulse minima at points (e.g., the starting points X) and determining if the BLP is stable enough to confidently compare pulse heights of a series of pulses.

Figure 6:
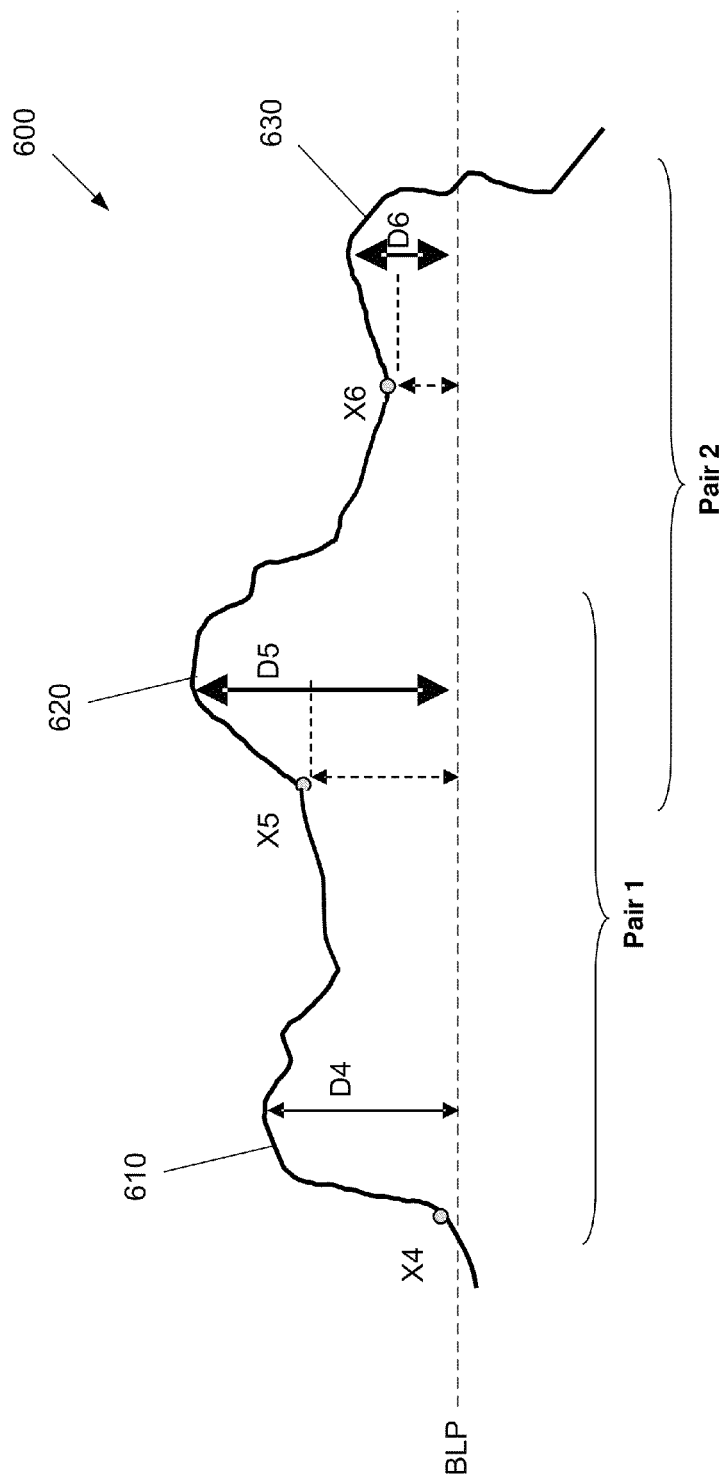
FIG. 6 shows another example oscillometric signal.

For example, referring now to FIG. 6, an example oscillometric signal 600 including three pulses 610, 620, 630 is shown.

The three pulses 610, 620, 630 are measured with an unstable BLP. Pulse heights D4, D5, and D6 are very different in measured amplitude even though the actual pulse height is consistent. The height measurements are incorrect due to the changing BLP.

In this situation, an algorithm monitoring pulse height regularity that assumes a static BLP would incorrectly identify the amount of irregularity as high. However, the pulse minima pressures at start points X4, X5, X6 can be analyzed to indicate instability in the BLP. Such an analysis can be used to indicate that the irregularity indication is impacted by an unstable BLP, thereby minimizing a potential for a false alarm for pulse height irregularity.

In an example embodiment, an algorithm compares the pressure differences in pulse minima to an average pulse height measurement of consecutive pulses. This ratio is compared to a threshold to determine if the pulse pair can be confidently used for pulse height variation evaluation. This ratio is referred to as the static baseline stability ratio (SBSR).

Figure 7:
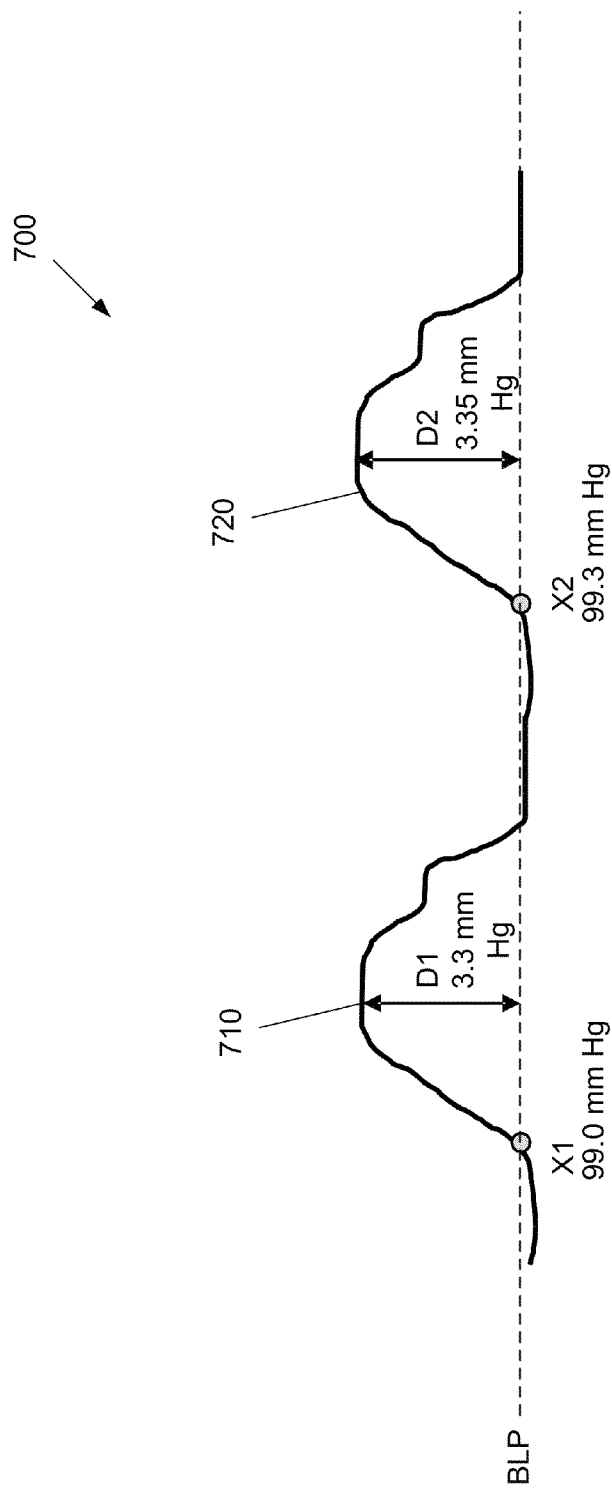
FIG. 7 shows another example oscillometric signal.

For example, referring now to FIG. 7, the BLP for the starting points X1 and X2 of two consecutive pulses 710, 720 of a pair 700 are analyzed. The SBSR1 for the pair 700 is calculated using Equation 1 as follows.

$$SBSR1 = \frac{\frac{D1+D2}{2}}{|X1-X2|} = \frac{\frac{3.30+3.35}{2}}{|99.0-99.3|} = \frac{3.325}{0.3} = 11.08$$

Since the difference between the BLP's at starting points X1 and X2 for the pair 700 is small, the resulting SBSR1 of 11.08 is large.

Figure 8:
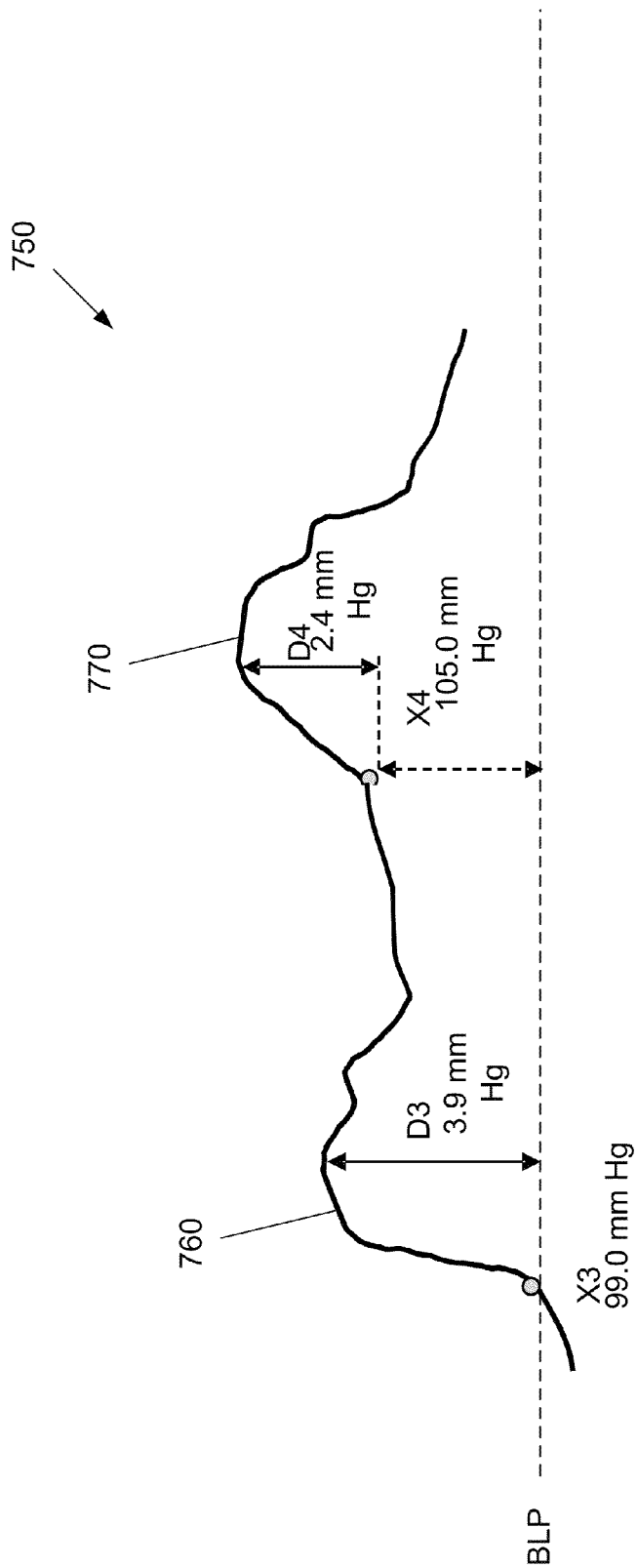
FIG. 8 shows another example oscillometric signal.

Referring now to FIG. 8, the BLP for the starting points X3 and X4 of two consecutive pulses 760, 770 of a pair 750 are analyzed. The SBSR2 for the pair 750 is calculated as follows.

$$SBSR2 = \frac{\frac{D1+D2}{2}}{|X1-X2|} = \frac{\frac{3.90+2.40}{2}}{|99.0-105.0|} = \frac{3.15}{6.0} = 0.53$$

Since the difference between the BLP's at starting points X3 and X4 for the pair 750 is large, the resulting SBSR2 of 0.53 is small.

In example embodiments, the calculated SBSR is compared to an SBSR threshold or limit to determine if the pulse pair is valid to use for pulse height irregularity determination. The SBSR limit can be a fixed ratio or a variable ratio that is dependent on the largest size pulse in the cycle or a user setting.

In one non-limiting example in which the SBSR limit is fixed, the SBSR is set to 5.0. This ratio limit caps the allowable baseline instability to less than 20% of the pulse height being measured. In such an example, the pair 700 would pass (since SBSR1>5.0) and the pair 750 would fail (since SBSR2<5.0). In such a scenario, the pair 700 could be used to evaluate pulse height irregularity, while the pair 750 could not. An alert to the caregiver of the device 200 can be provided when the pair 750 is measured (e.g., "An unacceptable amount of noise was detected in the recently-measured sample. Please redo this test.").

In another example, the SBSR limit is set as a variable limit. A variable limit may be desirable in some situations to reduce the occurrence of very small pulses being rejected too often. The use of a variable limit can be more sensitive to static pressure instability as the pulses get smaller. Examples of instances in which smaller pulses can be encountered are in small children or geriatric patients with calcified arteries.

In such scenarios, it may be advantageous to reduce the SBSR limit when the maximum pulse size across all cuff pressures is small. One non-limiting example of such a variable or dynamic ratio limit would allow the SBSR limit to decrease below 5.0 when the maximum pulse observed in the cycle is less than 1.0 mm Hg. An example SBSR variable limit calculation is show below in Equation 2.

SBSR Variable Limit=Maximum Pulse (mm Hg)×5

In this example, the SBSR Variable Limit is set at five times the maximum pulse height for the pulses included in the pair of pulses. Other equations to calculate the variable limit can be used.

In some examples, multiple pairs of pulses are measured at a given BLP. For example, as shown in FIG. 6, pair 1 (pulses 610, 620) and pair 2 (pulses 620, 630) are captured in the oscillometric signal 600. Both pairs 1 and 2 are available for heart beat variation evaluation. In this situation, adjacent pulse pairs 1 and 2 are each evaluated as discussed above, and the SBSR values are used to pick the best candidates for analysis. In an alternative example, the SBSR values of the pairs can be combined by averaging to determine if the entire group (e.g., including both pairs 1 and 2) is valid to use for heart beat variation evaluation.

In addition to multiple pairs of pulses measured at the same BLP, multiple pairs can be measured at different BLP values. In such a scenario, each pair can be analyzed to determine whether or not the pair should be included in the heart beat variation evaluation.

In other examples, more than two pulses can be evaluated to determine whether or not noise is present. For example, in another application, a trio of pulses is examined to determine whether or not sufficient noise is present to exclude the trio from the heart beat variation evaluation. Other configurations are possible.

Figure 9:
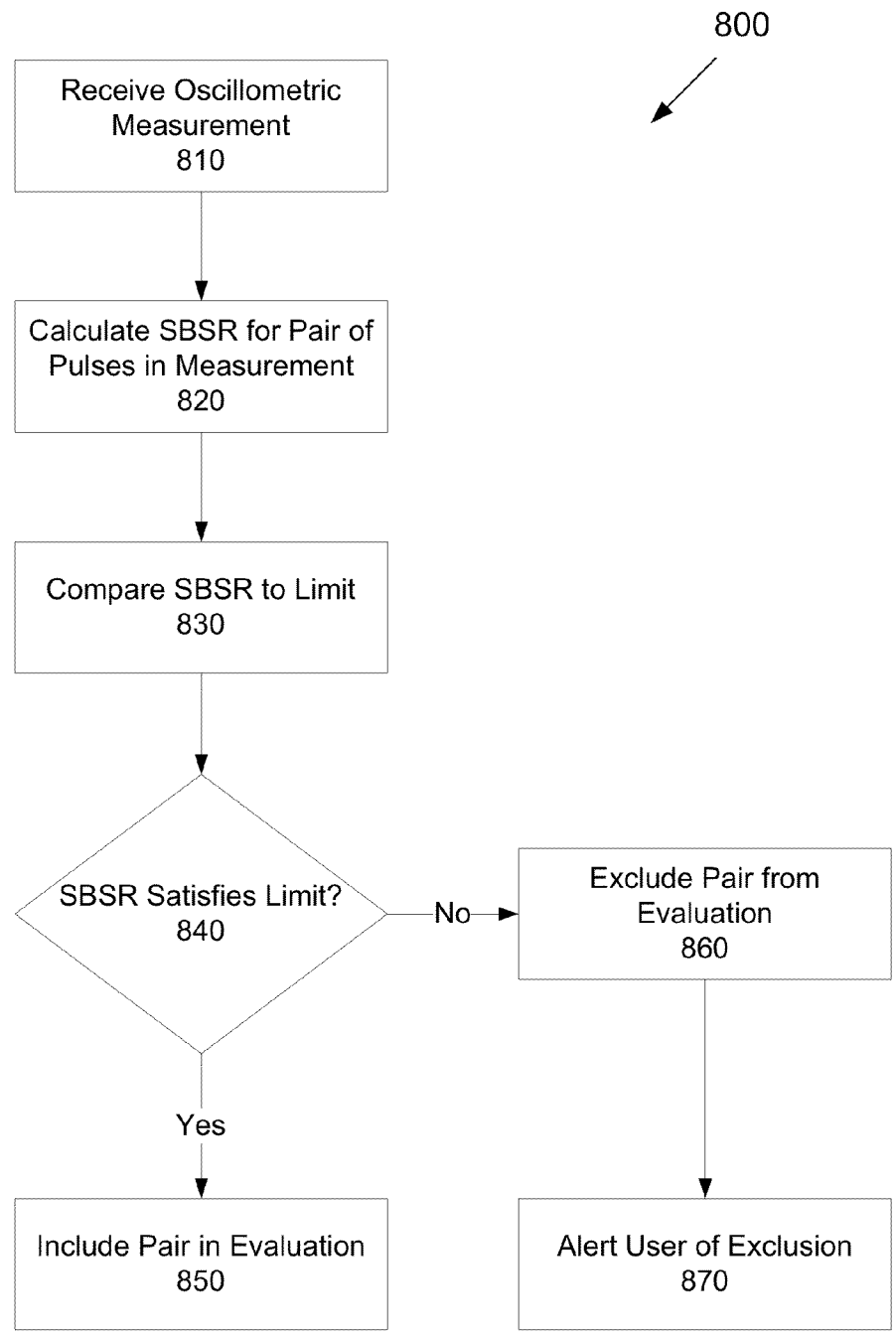
FIG. 9 shows an example method for detecting noise during heart beat variation evaluation.

Referring now to FIG. 9, an example method 800 is shown for detecting noise during heart beat variation evaluation.

Initially, at operation 810, the oscillometric measurements are received. For example, in one embodiment, the measurements are received at a device that is connected to a patient. In another example, the measurements can be received at a central server for processing.

Next, at operation 820, the SBSR for one or more pairs of pulses included in the oscillometric measurements are calculated. For example, the SBSR can be calculated using example Equation 1 above. Other methods for calculation can also be used.

Control is then passed to operation 830, at which the calculated SBSR for the one or more pairs of pulses is compared to a limit. This limit can be static or dynamically determined (see, e.g., Equation 2), as described above.

Next, at operation 840, a determination is made regarding whether or not the SBSR satisfies the limit. If so, control is passed to operation 850, and the pair is used in conjunction with the evaluation of heart beat variation.

If not, control is instead passed from operation 840 to operation 860, at which the pair is excluded from the evaluation.

Finally, at operation 870, the user can be alerted to the exclusion. For example, the interface for the device can display a message indicating that one or more pairs of pulses were excluded due to noise introduced during the measurements. In another example, the alert is displayed only if a sufficient number of pulses are excluded such that the evaluation of heart beat variation cannot be performed. In yet another example, the evaluation is performed using the available pulses, and an alert is provided with the results of the evaluation indicating that the results could have been impacted by noise. In such an example, the device can suggest that the user perform the measurements again.

Various embodiments disclosed herein can be implemented (1) as a sequence of computer implemented acts or program modules running on a computing system and/or (2) as interconnected machine logic circuits or circuit modules within the computing system. The implementation is a matter of choice dependent on the performance requirements of the computing system. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present disclosure.

Although the disclosure has been described in connection with various embodiments, those of ordinary skill in the art will understand that many modifications may be made thereto. Accordingly, it is not intended that the scope of the disclosure in any way be limited by the above description.

What is claimed is:

1. A physiological monitor device comprising:
a central processing unit (CPU) that is configured to control operation of the device;
at least one health care equipment module configured to measure one or more physiological parameters of a patient, the at least one health care equipment module including a non-invasive blood pressure module device configured to measure a blood pressure of the patient; and
a set of one or more computer readable data storage media storing software instructions that, when executed by the CPU, cause the device to:
obtain an oscillometric measurement associated with a patient's non-invasive blood pressure reading using the non-invasive blood pressure module;
determine a stability measure for at least one pair of pulses, including a first pulse and a second pulse, included in the oscillometric measurement, wherein the stability measure is a static baseline stability ratio (SBSR) according to a formula:

$$SBSR = \frac{\frac{D1 + D2}{2}}{|X1 - X2|}$$

wherein D1 and D2 are peak pressures of first and second pulses, and X1 and X2 are starting pressures of the first and second pulses;
compare the stability measure to a threshold; and
exclude the pair of pulses from an evaluation of heart beat variation when the stability measure fails to meet the threshold.

2. The device of claim 1, wherein the CPU further causes the device to alert a user when the pair of pulses is excluded from the evaluation of heart beat variation.

3. The device of claim 2, wherein the device further includes a display, and the alert is shown on the display.

4. The device of claim 1, wherein the CPU further causes the device to calculate the static baseline stability ratio by comparing an average of a peak pressure of each pulse in the pair of pulses to a difference in a starting pressure at a start of each pulse in the pair of pulses.

5. The device of claim 4, wherein the pair of pulses is excluded when the static baseline stability ratio is lower than the threshold.

6. The device of claim 1, further comprising a plurality of pulses, and wherein the CPU further causes the device to:
determine a stability measure for each pair of pulses in the plurality of pulses;
determine an average stability measure by averaging the stability measure for each pair of pulses in the plurality of pulses; and
compare the average stability measure to a threshold.

7. The device of claim 1, wherein the threshold is a static threshold.

8. The device of claim 1, wherein the threshold is a variable limit.

9. The device of claim 8, wherein the CPU further causes the device to calculate the variable limit as a multiple of a maximum pulse height of the pair of pulses.

10. A method for estimating noise associated with an evaluation of heart beat variation, the method comprising:
obtaining an oscillometric measurement associated with a patient's non-invasive blood pressure reading using a physiological monitor device, the physiological monitor device comprising:
a central processing unit; and
at least one health care equipment module configured to measure one or more physiological parameters of a patient, the at least one health care equipment module including a non-invasive blood pressure module device configured to measure a blood pressure of the patient;

determining a stability measure for at least one pair of pulses included in the oscillometric measurement using the physiological monitor device, wherein determining the stability measure includes:

calculating an average of a peak pressure of each pulse in the pair of pulses;

calculating a difference in a starting pressure at a start of each pulse in the pair of pulses; and comparing the average of the peak pressure of each pulse in the pair of pulses to the difference in the starting pressure at a start of each pulse in the pair of pulses to define a ratio;

comparing the stability measure to a threshold; and determining when the stability measure fails to meet the threshold.

11. The method of claim 10, further comprising alerting a user when the stability measure fails to meet the threshold.

12. The method of claim 10, further comprising excluding the pair of pulses when the ratio is less than the threshold.

13. The method of claim 10, further comprising calculating a variable limit to use as the threshold.

14. The method of claim 10, further comprising excluding the pair of pulses from the evaluation of heart beat variation when the stability measure fails to meet the threshold.

15. The method of claim 10, further comprising:

obtaining a first oscillometric measurement at a first baseline pressure;

obtaining a second oscillometric measurement at a second baseline pressure;

determining a first stability measure for a first pair of pulses in the first oscillometric measurement;

determining a second stability measure for a second pair of pulses in the second oscillometric measurement;

comparing the first and second stability measures to the threshold; and determining when the first and second stability measures fail to meet the threshold.

16. The method of claim 10, further comprising displaying a message to a user when the stability measure fails to meet the threshold.

17. A method for estimating noise associated with an evaluation of heart beat height variation using a physiological monitor device, the physiological monitor device comprising a central processing unit, and at least one health care equipment module configured to measure one or more physiological parameters of a patient, the at least one health care equipment module including a non-invasive blood pressure module device configured to measure a blood pressure of the patient, the method comprising:

obtaining an oscillometric measurement associated with a patient's non-invasive blood pressure reading using the non-invasive blood pressure module;

selecting at least one pair of pulses included in the oscillometric measurement;

calculating an average of a peak pressure of each pulse in the pair of pulses using the central processing unit;

calculating a difference in a starting pressure at a start of each pulse in the pair of pulses;

comparing the average of the peak pressure of each pulse in the pair of pulses to the difference in the starting pressure at the start of each pulse in the pair of pulses to define a stability ratio using the central processing unit;

comparing the stability ratio to a threshold;

determining when the stability ratio fails to meet the threshold;

excluding the pair of pulses when the stability ratio exceeds the threshold; and alerting a user using the physiological monitor device when the pair of pulses is excluded from the evaluation of heart beat height variation.

18. The method of claim 17, further comprising calculating a variable limit to use as the threshold.

* * * * *